(12) United States Patent
Seifert (10) Patent No.: US 10,146,907 B2
(45) Date of Patent: Dec. 4, 2018

(54) NETWORK SYSTEM AND METHOD FOR CONTROLLING A COMPUTER TOMOGRAPH

(71) Applicant: Siemens Aktiengesellschaft, Munich (DE)

(72) Inventor: Sascha Seifert, Koenigsbach-Stein (DE)

(73) Assignee: Siemens Aktiengesellschaft, Munich (DE)

( * ) Notice: Subject to any disclaimer, the term of this patent is extended or adjusted under 35 U.S.C. 154(b) by 694 days.

(21) Appl. No.: 14/688,116

(22) Filed: Apr. 16, 2015

(65) Prior Publication Data

US 2016/0004818 A1    Jan. 7, 2016

(30) Foreign Application Priority Data

Jul. 7, 2014 (EP) .................................. 14175985

(51) Int. Cl.
*G16H 40/67* (2018.01)
*G06F 19/00* (2018.01)
(Continued)

(52) U.S. Cl.
CPC ............ *G06F 19/321* (2013.01); *A61B 6/548* (2013.01); *A61B 6/566* (2013.01);
(Continued)

(58) Field of Classification Search
CPC ... G06F 19/3406; G06F 19/321; A61B 6/488; G16H 20/40
See application file for complete search history.

(56) References Cited

U.S. PATENT DOCUMENTS 6,335,979 B1 * 1/2002 Seto .................... G06F 19/3406
382/128
8,412,544 B2 4/2013 Reiner
(Continued)

FOREIGN PATENT DOCUMENTS

DE    102008002882 A1    1/2009
DE    102008002882 A1    1/2009
(Continued)

OTHER PUBLICATIONS

Du-Yih Tsai et al.: Information Entropy Measure for Evaluation of Image Quality, Journal of Digital Imaging, vol. 21, No. 3 Sep. 2008, pp. 338-347; 2008.
(Continued)

*Primary Examiner* — John A Pauls
(74) *Attorney, Agent, or Firm* — Harness, Dickey & Pierce, P.L.C.

(57) ABSTRACT

A computer network system and a method are disclosed for accessing a dose image database for medical imaging using ionizing radiation via an imaging device. An embodiment includes a multiplicity of imaging devices connected via a network connection to the dose image database, each imaging device including a transmit unit to transmit the images captured by the imaging device to the dose image database. An allocation between an image or a class of images, a dose measurement value, an image quality measurement value and optionally further medical metadata are stored in the dose image database. A control unit is included to exchange date with the dose image database and to generate control variables automatically while accessing the dose image database depending on at least one selection parameter to be defined, the parameters being forwarded via a network connection to at least one imaging device to control the imaging.

14 Claims, 3 Drawing Sheets

(51) Int. Cl.
- *A61B 6/00* (2006.01)
- *G06F 17/30* (2006.01)
- *G16H 40/63* (2018.01)
- *G16H 50/20* (2018.01)

(52) U.S. Cl.
CPC ...... *G06F 17/30598* (2013.01); *G06F 19/325* (2013.01); *G16H 40/63* (2018.01); *G16H 50/20* (2018.01)

(56) References Cited

U.S. PATENT DOCUMENTS

| | | | |
|---|---|---|---|
| 2009/0006131 A1 | 1/2009 | Unger et al. | |
| 2011/0311026 A1* | 12/2011 | Lalena | A61B 6/4405 378/98.5 |
| 2013/0243300 A1 | 9/2013 | Oda | |
| 2015/0199478 A1* | 7/2015 | Bhatia | A61L 36/488 382/128 |

FOREIGN PATENT DOCUMENTS

| | | |
|---|---|---|
| WO | WO-2012104786 A2 | 8/2012 |
| WO | WO 2012104786 A2 | 9/2012 |

OTHER PUBLICATIONS

Matthias Dorfer et al.: Constructing an Un-biased Whole Body Atlas from Clinical Imaging Data by Fragment Bundling, MICCAI 2013, Part I, LNCS 8149, pp. 219-226, Springer-Verlag Berlin Heidelberg 2013; 2013.

Cynthia M. McCollough et al. CT Dose Reduction and Dose Management Tools: Overview of Available Options, RadioGraphics 2006; vol. 26, No. 2, pp. 503-512, Radiological Society of North America; 2006.

M. Tapiavaara: Relationships between Physical Measurements and User Evaluation of Image Quality in Medical Radiology—A Review, STUK-A219, Sep. 2006, pp. 1-64, Helsinki, Finland; 2006.

Extended European Search Report dated Sep. 22, 2014.

* cited by examiner

NETWORK SYSTEM AND METHOD FOR CONTROLLING A COMPUTER TOMOGRAPH

PRIORITY STATEMENT

The present application hereby claims priority under 35 U.S.C. § 119 to European patent application number EP 14175985 filed Jul. 7, 2014, the entire contents of which are hereby incorporated herein by reference.

FIELD

At least one embodiment of the present invention lies within the fields of medical engineering, information technology and electronic controllers, and relates in particular to the control of imaging devices that use ionizing radiation for imaging.

BACKGROUND

Imaging medical devices use ionizing radiation in order to produce analyzable image data, such as e.g. computer tomographs or fluoroscopy devices. A fundamental aim is, wherever possible, to expose patients to only such a radiation dose that is absolutely essential in order to be able to guarantee an adequate image quality. The radiation dose to be applied and the image quality are in a competing relationship, so that the radiation dose is to be defined in each case through consideration of both aspects, which hinders an automatic control of the radiation dose. The dose definition is an important preparatory step in the planning, performance and/or control of the device in a radiotherapeutic or nuclear medical procedure.

Along with the consideration of how much of a dose reduction is achievable without having to accept interfering losses in image quality, the user is confronted with a multiplicity of examination parameters. Dose measurements are modality-specific measurement or estimation methods (e.g. for CT: volume CT dose index (CTDIvol), and dose length product (DLP); for fluoroscopy: dose area product (DAP), kerma area product (KAP), cumulative air kerma (CAK), and entrance surface dose (ESD) etc.). The effects of changes in one or more of these parameters on the image quality and dose often cannot be evaluated in a straightforward manner by the user. Moreover, there are manufacturer-specific parameters, the technical background of which is often not known in detail to the user. Dose optimization is also dependent on the type of imaging examination (modality employed and type of examination, such as e.g. thorax CT and abdomen CT).

In known methods, given this complexity, radiologists often rely on heuristics and empirical values in the creation of examination protocols. However, the quality assurance measures usable here are unfortunately very restricted. It is thus possible to implement institution-related quality assurance measures whereby, for example, radiologists define institution-related standards for examination protocols which are based on published studies of leading centers. However, all of these measures use either general (rather than case-specific) heuristics, concentrating on specific examination types or the evaluation of the dose (distribution) on the basis of phantom-based measurements (model-based dose measurements under controlled conditions that do not take into account the patient constitution and take only restricted account of anatomical structure details).

A patient-oriented, patient-specific and case-specific prediction and optimization of examination parameters for dose optimization is possible to a restricted extent only or is not at all possible on this basis. Heuristics allow the dose to be influenced within specific orders of magnitude, i.e. intervals are often indicated for examination parameters or fixed protocols which do not take any account or take only insufficient account of the hardware and software used and the special characteristics of the examination process. A first step in quality assurance often consists in the avoidance of outliers, i.e. of examinations in which an obviously excessively high dose is used and not in a fine-granularity dose optimization. Due to the high complexity of the relevant parameters, it is not possible for many examination variants simply to refer to publications that describe specifically adapted solutions for the current problem (complex combination of examination type, issues involved, patient constitution and equipment type).

Document US 2013/0243300 A1 relates to a system and method for radiographing management which manages radiographing information and provides support services for low-dose radiographing Document DE 10 2008 002882 A1 relates to the development of strategies for planning medical image data acquisition, the acquisition process, the processing of the image data and the display and visualization depending on access to an electronic patient file.

Document U.S. Pat. No. 8,412,544 B2 relates to a computer-implemented method for measuring a radiation dose and image quality in an imaging examination of a patient.

Document WO 2012/104786 A2 relates to a method which comprises an obtaining of electronically formatted information about previously performed imaging procedures and classifying the information into groups of protocols based on initially selected protocol groups.

SUMMARY

At least one embodiment of the present invention provides a network system with a dose image database for general exchange of dose-related datasets for medical imaging with ionizing radiation. For a pending imaging procedure, this is intended to enable the definition of optimum control variables for the case concerned with a calculation of a radiation dose. The intention is to enable the evaluation of the image quality of a multiplicity of preliminary examinations for this calculation On the whole, the radiation intensity for the patient in an imaging examination is intended to be reduced while maintaining an adequate image quality.

A method, a product (in particular also a computer program product) and a network system are disclosed.

Features, advantages or alternative embodiments mentioned here can also be transferred to the other claimed subject-matters and vice versa. In other words, the non-substantive claims (which relate, for example, to a method) can also be developed with the features described or claimed in connection with the system or network. The corresponding functional features of the method are formed by corresponding substantive modules, in particular by hardware modules.

According to one embodiment, the invention relates to a network system for providing a dose image database for medical imaging using ionizing radiation via an imaging device, comprising:

a multiplicity of imaging devices which are connected via a network connection to the dose image database, wherein each imaging device comprises a transmit unit which is intended to transmit all or selected images captured by the imaging device to the dose image database, wherein an allocation between an image or a class of images, a dose measurement value, an image quality measurement value and optionally also further medical metadata is stored in the dose image database a control unit which exchanges date with the dose image database and serves to generate control variables automatically while accessing the dose image database depending on at least one selection parameter to be defined, said parameters being forwarded via a network connection to at least one imaging device to control the imaging.

The terms used in connection with this application are explained in detail below.

A computer program product is further disclosed. A computer program comprising computer instructions is disclosed. The computer instructions are stored on a memory of a computer and comprise commands readable by the computer which are intended to carry out the method described above when the commands are executed on the computer. The computer program may also be stored on a storage medium or may be downloaded from a server via a corresponding network.

A computer-implemented method is further disclosed for exchanging control variables for an imaging device for imaging with ionizing radiation while accessing a dose image database, comprising:

automatic transmission of all or selected images which are captured by one or more imaging devices via a network connection to a dose image database, creation of an allocation and storage thereof in the dose image database between an image or a class of images, a dose measurement value, an image quality measurement value and optionally also further medical metadata creation of control variables depending on at least one selection parameter to be defined while accessing the dose image database, forwarding of the generated control variables via a network connection to at least one imaging device to control the imaging.

BRIEF DESCRIPTION OF THE DRAWINGS

In the following detailed description of the figures, example embodiments with their features and further advantages are discussed with reference to the drawing in a manner which is to be understood as non-limiting. In the drawing.

The invention is explained in detail below on the basis of example embodiments with reference to the attached figures.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The network system is computer-based. In the preferred embodiment, it comprises a plurality of computing units, processors, computers and/or networks. It may be a local area network (LAN) and/or a wide area (WAN) with corresponding intermediate systems, such as switches, packet switches, bridges and routers. The LAN may be operated and implemented within one institution or across institutions in order to connect a plurality of different clinical areas. Correspondingly, according to one embodiment, the network connection may be a LAN connection or, according to an alternative embodiment, a WAN connection. The latter can also be implemented via an Internet connection or a mobile radio connection.

The network system serves to provide the dose image database. In addition, it can also be used to access the dose image database. The access may be WRITE, READ or EXE.

The imaging device is a medical engineering device for image acquisition. In one preferred embodiment, the image acquisition is effected using ionizing radiation, such as, for example, by means of a computer tomograph, computer radiography device, X-ray appliance, tomosynthesis device and/or fluoroscopy devices. In a broader sense, other devices which require a dose definition can also be controlled with the method according to the invention.

Control variables (also referred to as control parameters) are parameters which have to be set when the medical device is used. According to one aspect, radiation dose data are also comprised of control variables. The definition of a reconstruction algorithm, the table feed or further technical device parameters are also included. The control variables are the settings that are used in a future or planned application of ionizing radiation, the dose of which is to be determined and used to control the device.

The control unit serves to calculate the control variables which are forwarded from it to the relevant imaging devices. The control unit may also be designed as a dose definition unit and may therefore have a restricted functionality in order to define the dose for a pending examination, referring back to a calculation based on a multiplicity of previous images and the evaluation of the image quality of said images. Furthermore, the control unit can also automatically define a protocol for the imaging device and the pending examination, and, where relevant, can automatically apply them after receiving a confirmation signal.

The control unit may furthermore be designed additionally to comprise or to access a visualization unit, wherein the visualization unit is intended to visualize images or reference images taken into consideration by the control unit. This offers the advantage that a user can directly see which images have been used as reference images for dose definition and for calculating the control variables.

In one embodiment, the control unit can be disposed directly in the dose image database or can be connected as a separate computer-based instance to the dose image database, but not implemented therein, and can be centrally provided for all imaging devices (e.g. in a cloud or in a data center). In an alternative embodiment, the control unit can also be designed as a local and distributed unit, and can be provided on all or on selected imaging devices. It is also possible to define selected imaging devices on which the control unit is installed, which then serves for the other imaging devices, in a manner of speaking, as a transmit instance for transmitting control parameters.

All dose-related information is stored in the dose image database. This information is constantly updated (continuously or, according to one preferred embodiment, on the basis of predefined (time-based or event-based) criteria. An allocation between an image or a class of images, a dose measurement value, an image quality measurement value and optionally also further medical metadata is stored in the dose image database. For the class of images, all images having comparable values for the definition of the dose can form a class or group. Thus, for example, images of a study can be combined in respect of their quality and the allocation relationship needs to be stored in a memory-space-saving manner for only one image representative of the group. A reference can automatically be stored, indicating that the same allocation also applies to the other images from the same class.

As already mentioned above, an imaging device normally comprises a transmit unit. The transmit unit is intended to transmit all or selected images captured by the imaging device to the dose image database. It is similarly possible that not all—as provided in the preferred embodiment— imaging devices transmit their images to the dose image database, but, here also, specific imaging devices can again be selected (in particular with a good network connection and/or sufficient computing power, and this can also be defined as dynamically variable), which can operate as transmitters for the images to the central dose image database of other modalities.

Radiation dose data are the total quantity of radiation data acquired from past and present applications of ionizing radiation. The radiation dose recorded per time unit is referred to as the dose rate (unit: Sv/s or Sv/h).

According to one embodiment, the invention therefore relates to a system for controlling an imaging device via control variables which evaluate the image quality and radiation dose in combination. This is performed on the basis of the evaluation of stored images (or extracts thereof) in that their image quality is determined for the relevant applied radiation dose and/or the acquisition parameters (control variables) used.

The aim is to achieve a dose reduction while ensuring an image quality that is adequate for the respective examination. The image quality is preferably analyzed as adequate or inadequate on the basis of automatically evaluated reference images. According to at least one embodiment of the invention, the quantity of the physical radiation dose can advantageously be reduced without having to accept an associated loss of image quality.

According to one preferred embodiment, the network system comprises a clustering unit which is intended to define a reference image (as an image representative) for a set of images. This has the advantage that only the allocation relationship for the reference image needs to be stored in the dose image database. It is automatically defined that the same allocation relationship applies to all other images of the class/cluster.

The selection parameters are formed from a set of parameters and may comprise one or more of the following parameters:
  patient identity
  anatomical area to be examined
  required image quality
  further metadata which, according to one preferred variant of the invention, can be read automatically from the DICOM header (DICOM: Digital Imaging and Communications in Medicine).

The network system may additionally comprise a quality definition unit which is intended to automatically define the image quality measurement value. Image-processing algorithms can be used for this purpose.

A computer-implemented method is further disclosed for exchanging control variables for an imaging device for imaging with ionizing radiation while accessing a dose image database, comprising:
  automatic transmission of all or selected images which are captured by one or more imaging devices via a network connection to a dose image database,
  creation of an allocation and storage thereof in the dose image database between an image or a class of images, a dose measurement value, an image quality measurement value and optionally also further medical metadata
  creation of control variables depending on at least one selection parameter to be defined while accessing the dose image database,
  forwarding of the generated control variables via a network connection to at least one imaging device to control the imaging.

The method comprises two phases separated from one another: an image collection phase in which the images are collected and, where appropriate, processed by the modalities and are stored in the dose image database, and a control phase in which, while accessing the database, control variables are derived and calculated and are used to control the devices. The two phases are independent from one another.

The first phase of image collection is in principle carried out before the second control phase. However, it is also within the scope of the invention to perform the aforementioned steps of the method not necessarily in the sequence described above. Alternatively, it is also possible, for example, to interlock the two phases so that the image data from a second device are also collected and supplied to the system during the control, for example, of a first device.

The method steps of reading in the image data and acquiring control variables can be interleaved so that, in the presentation of image data, a window can be activated directly on the monitor of the diagnostic system via which control data relating to the respectively presented images can be entered. This window can be activated either for one image for or a group of images (e.g. a series of images from an examination), e.g. via a mouse click.

In addition, it is possible for individual phases of the method described above to be formed as individual saleable units and the remaining phases of the method can be formed as other saleable units. The method according to an embodiment of the invention can thus be implemented as a distributed system on different computer-based instances (e.g. client-server instances). It is thus possible, for example, for the control unit for its part to comprise different sub-modules which are partially implemented on the respective imaging device, partially on the dose image database and/or partially on other computer-based instances.

Figure 1:
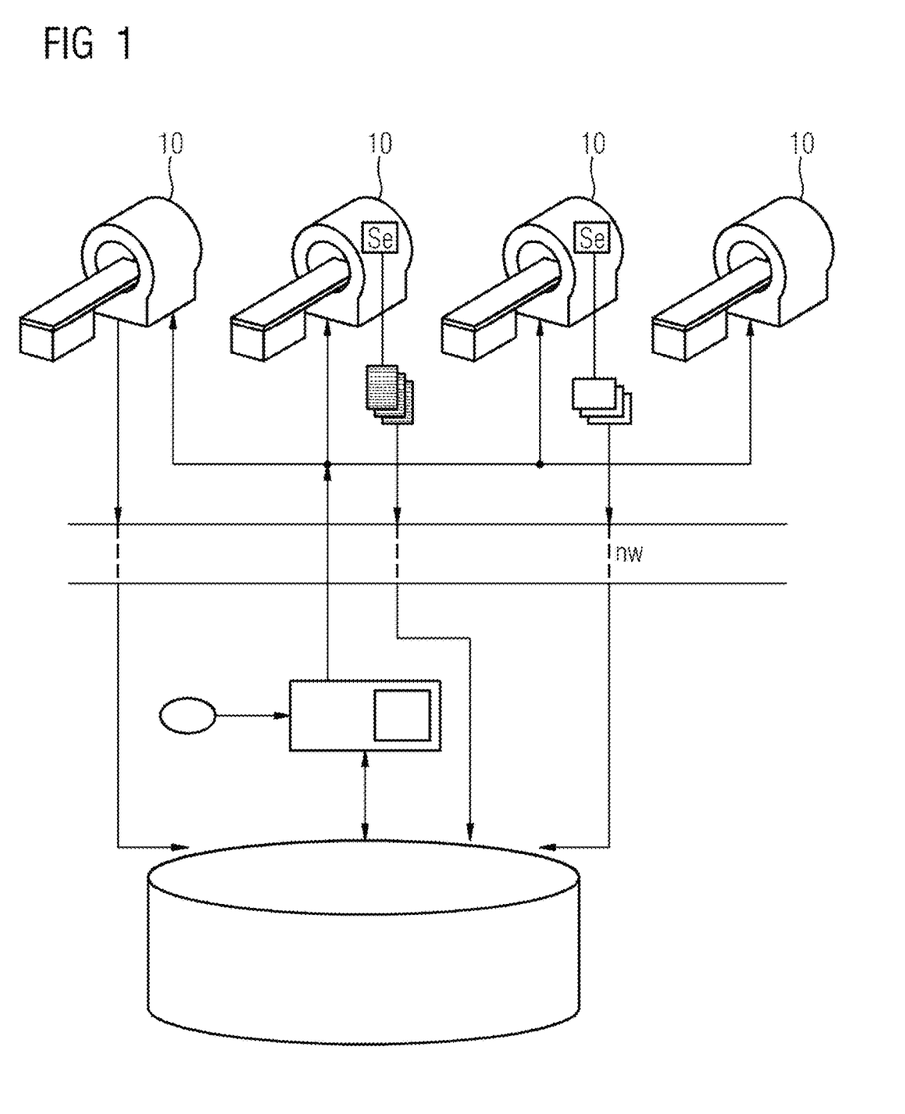
FIG. 1 shows a schematic representation of a system according to an embodiment of the invention with a dose image database and further instances according to one example embodiment.

An embodiment of the invention relates to a network system which is shown schematically in FIG. 1. A plurality of imaging devices (CT, conventional X-ray, MRT, PET, ultrasound, etc.), also referred to as modalities 10, may exchange data with one another and with further electronic units via one or more networks nw. The network system is designed for crowdsourcing. This makes it possible to collect dose-related information from many devices and users, to cluster this information and automatically derive control information, particularly relating to a dose setting, from said information by means of learning algorithms. Through the crowdsourcing aspect, each connected unit or each participant in the network system learns and can benefit therefrom. By querying a central dose image database DDB, better settings can thus be found automatically for the respective device. "Better settings" relates in particular to a dose reduction which can be achieved only on the basis of an automatic image analysis of the images. The modalities 10 transmit the image data or images acquired by them via the network nw to the dose image database DDB. The dose image database DDB stores images and dose measurement values, quality measurement values and further data allocated thereto and holds them ready for access. The data can be retrieved with different keys. The database DDB exchanges data with the control unit S which, in one variant, may comprise a visualization unit V. The visualization unit V serves to display images on a display device; the latter may also be provided separately from the visualization unit V and/or from the control unit S, e.g. on one of the imaging devices 10. The advantage thus exists for the user that he can see the images whose quality has been measured and taken into account in calculating the dose, and can therefore also understand the calculation or the basis of the calculation. The plausibility of the control can be checked with this feature. Furthermore, the visualization unit V can also serve to display the calculated control variables with the calculated dose, which in turn enables an additional check and can therefore increase the overall quality.

An allocation relationship is stored in the dose image database DDB. For each image or for a class of images, it comprises:
dose information or a dose measurement value,
image quality information or an image quality measurement value.

In further developments of an embodiment of the invention, it is helpful to provide still further data, such as:
the respective anatomical region of the body (skull, knee, heart, etc.),
the status of the image data (child, adult), and/or
where relevant, further data that can also be read automatically from the DICOM header and processed.

Each or selected imaging device(s) 10 preferably comprise a transmit unit Se which is intended to transmit the images acquired by the imaging device 10 to the dose image database DDB as soon as the latter is available as an image dataset. The transmit unit Se can be controlled according to different patterns. All images are preferably transmitted automatically to the dose image database DDB. It is also possible to operate the transmit unit Se in a pooling mode and first collect a configurable number of image datasets and then forward them as a packet to the database DDB.

The method according to an embodiment of the invention will be explained in detail below according to a preferred embodiment with reference to FIG. 2.

After the start of the method, the image data acquired and, where relevant, calculated on the modality 10 are transmitted in step 100 to the dose image database DDB.

In step 200, an allocation relationship is created in and for the database DDB. Further datasets are allocated to each image or to a class of similar images. As already described above, these records comprise at least dose information and image quality information.

This allocation is stored in step 300.

The image data are normally acquired in DICOM format as so-called studies, which in each case comprise a multiplicity of images, e.g. a set of layered image recordings for a three-dimensional dataset. For a study of this type or for a different set of images, a substitute can be defined as a representative image for the class. The image class representative is intended to characterize the set of images in this class or group. The criteria for the class formation are variable and can be adapted on a case-by-case basis. In one preferred embodiment, the class formation is effected in the clustering unit, which is denoted by the reference number 70. The clustering unit 70 can be incorporated into the database or can be connected to it via a network connection nw.

The control variables for the pending examination are generated in step 400. In one preferred embodiment, the control variable is a dose parameter. Alternatively, it may comprise further control parameters.

In step 500, the calculated control variables are forwarded to the respective modalities 10 and are distributed. It is possible here for the control variables to be calculated simultaneously and, in a manner of speaking, in parallel for a plurality of modalities 10. The control parameters are then modality-specific and are forwarded to the respectively relevant modality via an identifier allocated to the control dataset.

Figure 2:
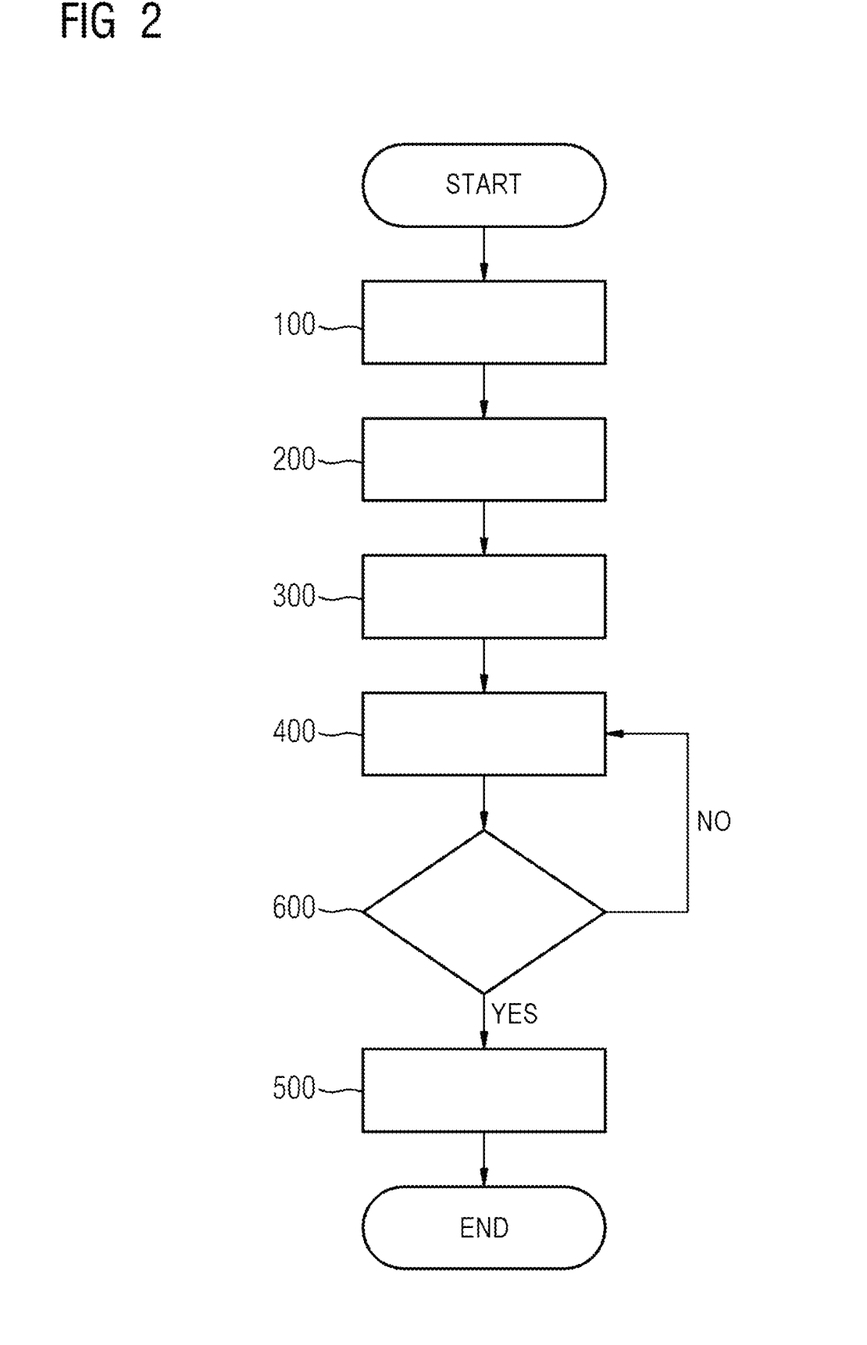
FIG. 2 shows a flow chart of a method according to one preferred embodiment of the invention.

As shown in FIG. 2, it can be provided in one variant of an embodiment of the invention that the calculated control variables are validated/confirmed or rejected in step 600 by a confirmation signal of a user. In the case of confirmation, the method continues with step 500. In the case of rejection, the method can end, or step 400 can again be carried out with the generation of control variables.

Figure 3:
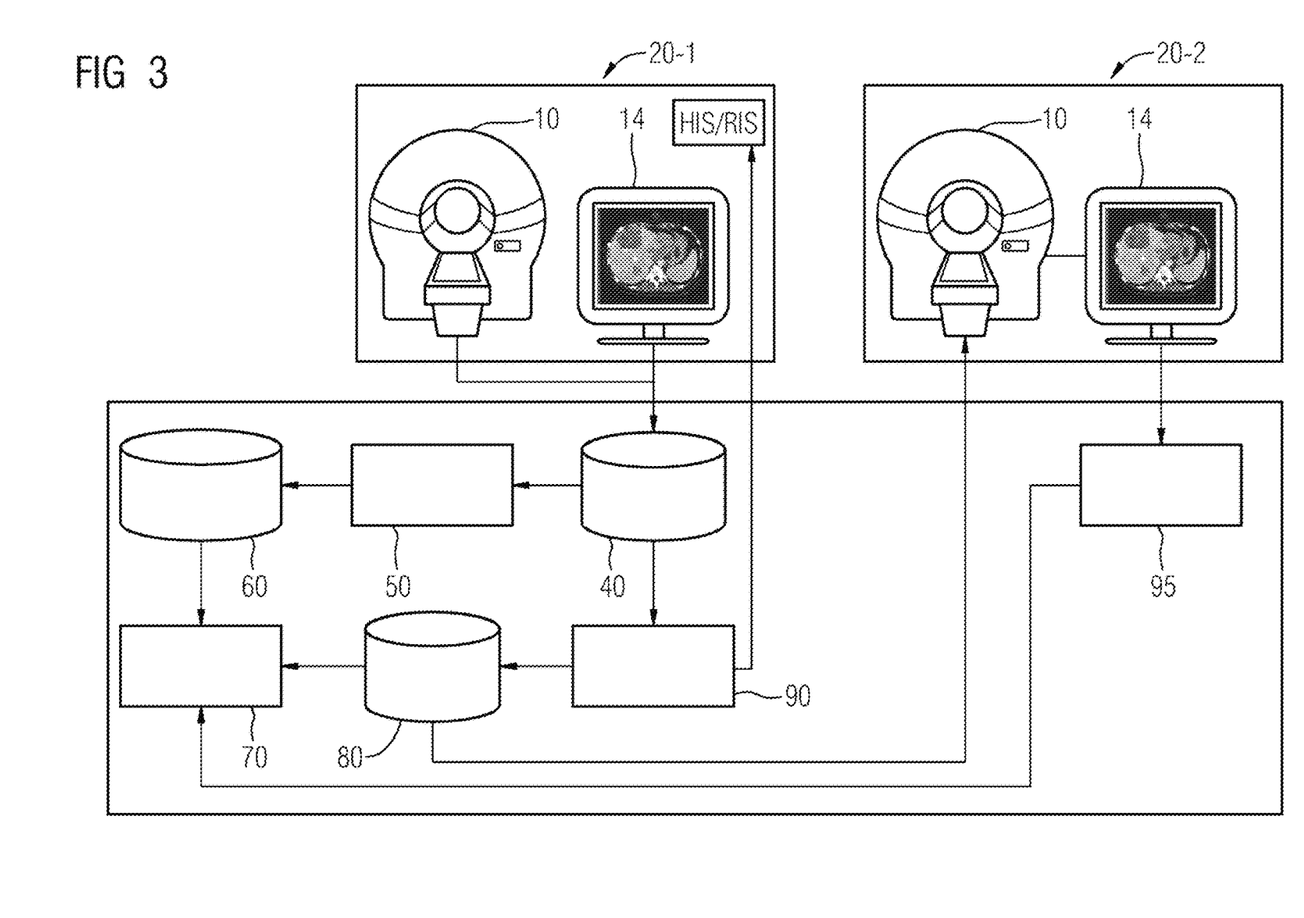
FIG. 3 shows an overview presentation of the network with further units and instances according to one example embodiment of the invention.

FIG. 3 shows a variant of the network with further instances in a schematic representation. In this case, the modalities 10 are computer tomographs, which are shown in FIG. 3, above. The modalities 10 exchange data with a workstation 14 and the latter can also exchange data with a radiology information system RIS and/or with a hospital information system HIS. FIG. 3 in each case shows two modalities only; a plurality of modalities 10 are normally interconnected to form a site 20-1, 20-2. The CT modality 10 (the scanner) or the allocated workstation 14 automatically loads the images acquired by it into a cloud-based network system, in particular into an image database 40.

An image features extractor 50, (which can also be referred to as a quality definition unit; in this context, these two terms are to be understood as synonymous) accesses this image database 40 in order to run an image-processing algorithm (for the extraction of image features) on all or selected images stored in the image database. The extracted features serve to calculate an image quality. The image quality can, in particular, be calculated by algorithms which characterize a distinguishability of anatomical structures (e.g. organs) from the image background (e.g. surrounding tissue), referred to as smoothness. In addition, a signal-to-noise ratio (S/N ratio) can be calculated. The extracted features which characterize the image quality are stored in an image features database 60. In addition, meta information on the patient can also be stored, such as e.g. shape/girth, size, gender, status (male/female), etc.

The dose data extractor 90 accesses the radiology information system RIS and/or the hospital information system HIS in order to acquire datasets relating to the disease of the patient. In addition, further anatomical or medical background information which is relevant to the dose calculation can be read out. Furthermore, the protocol on which the relevant recording is based and the radiation dose data are read out from an image dataset allocated to the image (preferably from the DICOM header). These dose metadata are stored in a dose registry 80, which can also be organized as a database. In one preferred embodiment, the dose data registry 80 corresponds to the dose image database DDB. However, it is also possible to provide different instances here.

A clustering unit 70 accesses the image features stored in the image features database 60 and classifies the images into classes (image classes) or groups. To do this, it preferably uses a multi-class training algorithm in order to define similar cases with similar images and similar dose measurement values (settings and protocols). These training results calculated in this way are then returned to the dose registry 80 for storage. In addition, the clustering unit 70 calculates representative images and dose settings for each cluster (class), which can then be used later in a dose definition phase (query phase). The parameters relevant to the dose calculation can thus be constantly or continuously refined. The quality for controlling the device in terms of the dose to be set can thus be significantly increased.

Later, during the dose definition phase, a different site 20-n can, for example, access the dose registry 80 and search the dataset stored there by means of a query unit 95 by searching automatically in the clustering unit 70 for suitable representative images in order to automatically calculate an optimum setting therefrom with the appropriate control variables for the pending examination. Following the calculation, the respective protocol can then be loaded automatically from the dose registry 80 onto the scanner and applied. However, the network system is also intelligent enough to proactively generate protocol settings as control variables. To do this, in one simple embodiment of the invention, an evaluation algorithm can be applied in order to automatically determine control variables and dose target values from the metadata (illness of the patient) and the required procedure (e.g. skull CT).

In addition, the user can define the relevant protocol with the dose calculation via the selection of images. In this case, he characterizes (e.g. highlights) the images or representative images that he deems to be of adequate quality (or best-suited). The respectively allocated dose report (which may be stored in the dose registry 80) is then automatically opened by the system in order to define the dose. The respective control parameters can then be transferred in order to define the dose value for the pending examination. This selection facility based on the images is highly advantageous for the user, since he only needs to find his way round the images and does not need to carry out any further mental conversions (e.g. in the form of numbers or other metrics). He can simply select the reference image (from the set of previous recordings stored in the database) which he deems to be of adequate quality. The respectively allocated dose is defined automatically for this reference image and is output as the target radiation dose.

It should finally be pointed out that the description of the invention and the example embodiments are essentially not to be understood as limiting in terms of a specific physical implementation of the invention. It is particularly obvious to a person skilled in the art that the invention can be partially or totally implemented in software and/or hardware and/or can be distributed among a plurality of physical products, also including, in particular, computer program products, e.g. on the modality side (client site side) or centrally (dose image database side or host side).

REFERENCE NUMBER LIST

10 Imaging device (modality)
20 Site, network unit
20-1 First site
20-2 Second site
HIS Hospital Information System
RIS Radiology Information System
14 Workstation
40 Image database
50 Image features extractor
60 Image features database
70 Clustering unit
80 Dose registry
90 Dose data extractor)
95 Query unit
ap Selection parameter
S Control unit
V Visualization unit
DDB Dose image database
Nw Network
100 Automatic transmission of all or selected images
200 Creation of an allocation or allocation relationship
300 Storage of the allocation
400 Generation of control variables
500 Forwarding of the generated control variables
600 User validation/signal input: Has confirmation signal been received?

What is claimed is:

1. A computer-implemented network system for accessing a dose image database, the computer-implemented network system comprising:
a plurality of imaging devices, connected via a network connection to the dose image database, each of the plurality of imaging devices,
being configured to capture at least one image using ionizing radiation, and
including a transmitter configured to transmit the at least one image captured by the respective imaging device to the dose image database;
the dose image database configured to store a plurality of images received from at least one of the plurality of imaging devices, the plurality of images including a plurality of reference images, each of the plurality of images being stored in association with a dose measurement value, an image quality measurement value, and at least one selection parameter; and
at least one processor configured to execute computer-readable instructions stored in a memory to,
assign each respective image among the plurality of images stored by the dose image database to a class among a plurality of classes based on the image quality measurement value and the dose measurement value associated with the respective image,
cause display of the plurality of reference images stored by the dose image database, each of the plurality of reference images being assigned to a different class of the plurality of classes,
receive a selection of a subset of the displayed plurality of reference images,
generate radiation dose data by querying the dose image database based on the subset of the displayed plurality of reference images and at least one defined selection parameter to identify one or more dose measurement values, and
control an image capture performed by at least one of the plurality of imaging devices by forwarding the generated radiation dose data to the at least one of the plurality of imaging devices.

2. The computer-implemented network system of claim 1, wherein the at least one processor is external to the plurality of imaging devices.

3. The computer-implemented network system of claim 2, wherein the at least one processor is further configured to execute computer-readable instructions stored in the memory to define an image quality measurement value of an image captured by an imaging device among the plurality of imaging devices.

4. The computer-implemented network system of claim 2, wherein the at least one processor is further configured to execute computer-readable instructions stored in the memory to control the image capture performed by the at least one of the plurality of imaging devices in response to receiving a confirmation signal.

5. The computer-implemented network system of claim 2, further comprising at least one display configured to display the plurality of reference images.

6. The computer-implemented network system of claim 1, wherein one or more of the at least one processor is included in each of the plurality of imaging devices.

7. The computer-implemented network system of claim 1, wherein
the at least one processor is further configured to execute computer-readable instructions stored in the memory to define the plurality of reference images, each of the plurality of reference images corresponding to a set of images captured by one or more of the plurality of imaging devices.

8. The computer-implemented network system of claim 1, wherein the at least one defined selection parameter includes one or more of,
a patient identity,
an anatomical area to be examined, or
a required image quality.

9. The computer-implemented network system of claim 1, wherein the at least one processor is further configured to execute computer-readable instructions stored in the memory to define an image quality measurement value of an image captured by an imaging device among the plurality of imaging devices.

10. The computer-implemented network system of claim 1, wherein the at least one processor is further configured to execute computer-readable instructions stored in the memory to,
cause display of the generated radiation dose data,
control the image capture performed by the at least one of the plurality of imaging devices in response to receiving a confirmation signal, the confirmation signal being received after the display of the generated radiation dose data,
cause re-display of the plurality of reference images, in response to receiving a rejection signal, the rejection signal being received after the display of the generated radiation dose data,
receive a different selection of the subset of the re-displayed plurality of reference images, and
generate updated radiation dose data based on the different selection.

11. The computer-implemented network system of claim 1, further comprising at least one display configured to display the plurality of reference images.

12. The computer-implemented network system of claim 1, wherein the dose image database is further configured to store the plurality of images received from the at least one of the plurality of imaging devices in association with the dose measurement value, the image quality measurement value, the at least one selection parameter, and medical metadata.

13. A computer-implemented method for controlling image capture, the method comprising:
transferring a plurality of images captured by one or more imaging devices to a dose image database via a network connection, the plurality of images including a plurality of reference images;
storing the plurality of images in the dose image database, each of the plurality of images being stored in association with a dose measurement value, an image quality measurement value, and at least one selection parameter;
assigning each respective image among the plurality of images stored in the dose image database to a class among a plurality of classes based on the image quality measurement value and the dose measurement value associated with the respective image;
displaying the plurality of reference images stored in the dose image database, each of the plurality of reference images being assigned to a different class of the plurality of classes;
receiving a selection of a subset of the displayed plurality of reference images;
generating radiation dose data by querying the dose image database based on the subset of the displayed plurality of reference images and at least one defined selection parameter to identify one or more dose measurement values; and controlling an image capture performed by at least one of the one or more imaging devices by forwarding the generated radiation dose data to the at least one of the one or more imaging devices.

14. A non-transitory computer-readable medium storing instructions that, when executed by at least one processor, cause the at least one processor to:

transfer a plurality of images captured by one or more imaging devices to a dose image database via a network connection, the plurality of images including a plurality of reference images;

store the plurality of images in the dose image database, each of the plurality of images being stored in association with a dose measurement value, an image quality measurement value, and at least one selection parameter;

assign each respective image among the plurality of images stored in the dose image database to a class among a plurality of classes based on the image quality measurement value and the dose measurement value associated with the respective image;

display the plurality of reference images stored in the dose image database, each of the plurality of reference images being assigned to a different class of the plurality of classes;

receive a selection of a subset of the displayed plurality of reference images;

generate radiation dose data by querying the dose image database based on the subset of the displayed plurality of reference images and at least one defined selection parameter to identify one or more dose measurement values; and control an image capture performed by at least one of the one or more imaging devices by forwarding the generated radiation dose data to the at least one of the one or more imaging devices.

* * * * *